(12) United States Patent
Xie et al.

(10) Patent No.: US 11,900,602 B2
(45) Date of Patent: *Feb. 13, 2024

(54) SYSTEM AND METHOD FOR MEDICAL IMAGING

(71) Applicant: SHANGHAI UNITED IMAGING HEALTHCARE CO., LTD., Shanghai (CN)

(72) Inventors: Huifang Xie, Shanghai (CN); Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,331

(22) Filed: Mar. 6, 2023

(65) Prior Publication Data

US 2023/0206442 A1     Jun. 29, 2023

Related U.S. Application Data

(63) Continuation of application No. 16/854,838, filed on Apr. 21, 2020, now Pat. No. 11,599,995.

(30) Foreign Application Priority Data

Apr. 24, 2019    (CN) .......................... 201910335013.7

(51) Int. Cl.
*G06T 7/00*      (2017.01)
*G06T 5/50*      (2006.01)
(Continued)

(52) U.S. Cl.
CPC ............ *G06T 7/0012* (2013.01); *A61B 5/055* (2013.01); *A61B 6/032* (2013.01); *A61B 6/037* (2013.01);
(Continued)

(58) Field of Classification Search
CPC ......... G06T 7/0012; G06T 5/002; G06T 5/50; G06T 11/005; G06T 2207/10081;
(Continued)

(56) References Cited

U.S. PATENT DOCUMENTS 10,679,385 B1 *  6/2020  Yanoff ................... G01T 1/1663
10,685,461 B1 *  6/2020  Chan ..................... G06T 11/006
(Continued)

FOREIGN PATENT DOCUMENTS

CN      105118078 A     12/2015
CN      106683146 A      5/2017

*Primary Examiner* — Siamak Harandi
(74) *Attorney, Agent, or Firm* — METIS IP LLC

(57) ABSTRACT

The present disclosure provides a system and method for medical imaging. The method may include obtaining a preliminary image and scanning data of a subject acquired using a scanner. The method may also include determining a regularization parameter for a regularization item of an objective function based at least in part on the scanning data, wherein the regularization parameter includes at least two of a first component characterizing quality of the scanning data, a second component characterizing the scanner, or a third component characterizing a feature of the subject. The method may further include generating an image of the subject by reconstructing the preliminary image based on the objective function.

20 Claims, 11 Drawing Sheets

(51) Int. Cl.
*A61B 5/055* (2006.01)
*A61B 6/03* (2006.01)
*A61B 6/00* (2006.01)
*G06T 5/00* (2006.01)
*G06T 11/00* (2006.01)

(52) U.S. Cl.
CPC .......... *A61B 6/5235* (2013.01); *A61B 6/5247* (2013.01); *A61B 6/5258* (2013.01); *G06T 5/002* (2013.01); *G06T 5/50* (2013.01); *G06T 11/005* (2013.01); *G06T 2207/10081* (2013.01); *G06T 2207/10088* (2013.01); *G06T 2207/10104* (2013.01); *G06T 2207/20182* (2013.01)

(58) Field of Classification Search
CPC . G06T 2207/10088; G06T 2207/10104; G06T 2207/20182; G06T 2207/30016; G06T 11/003; A61B 5/055; A61B 6/037; A61B 6/5235; A61B 6/5247; A61B 6/5258; A61B 6/032; A61B 6/5205
See application file for complete search history.

(56) References Cited

U.S. PATENT DOCUMENTS

| | | |
|---|---|---|
| 2014/0226887 A1 | 8/2014 | Takahashi et al. |
| 2017/0294034 A1* | 10/2017 | Zhou ..................... G06T 11/008 |
| 2020/0105032 A1* | 4/2020 | Yang ....................... G06T 5/002 |
| 2020/0311878 A1* | 10/2020 | Matsuura ............. G06V 10/764 |
| 2020/0334869 A1* | 10/2020 | Yu .......................... G06T 7/0012 |
| 2021/0312622 A1* | 10/2021 | Buckler ............ G06F 18/24143 |
| 2022/0172328 A1* | 6/2022 | Reader ..................... G06T 5/50 |

\* cited by examiner

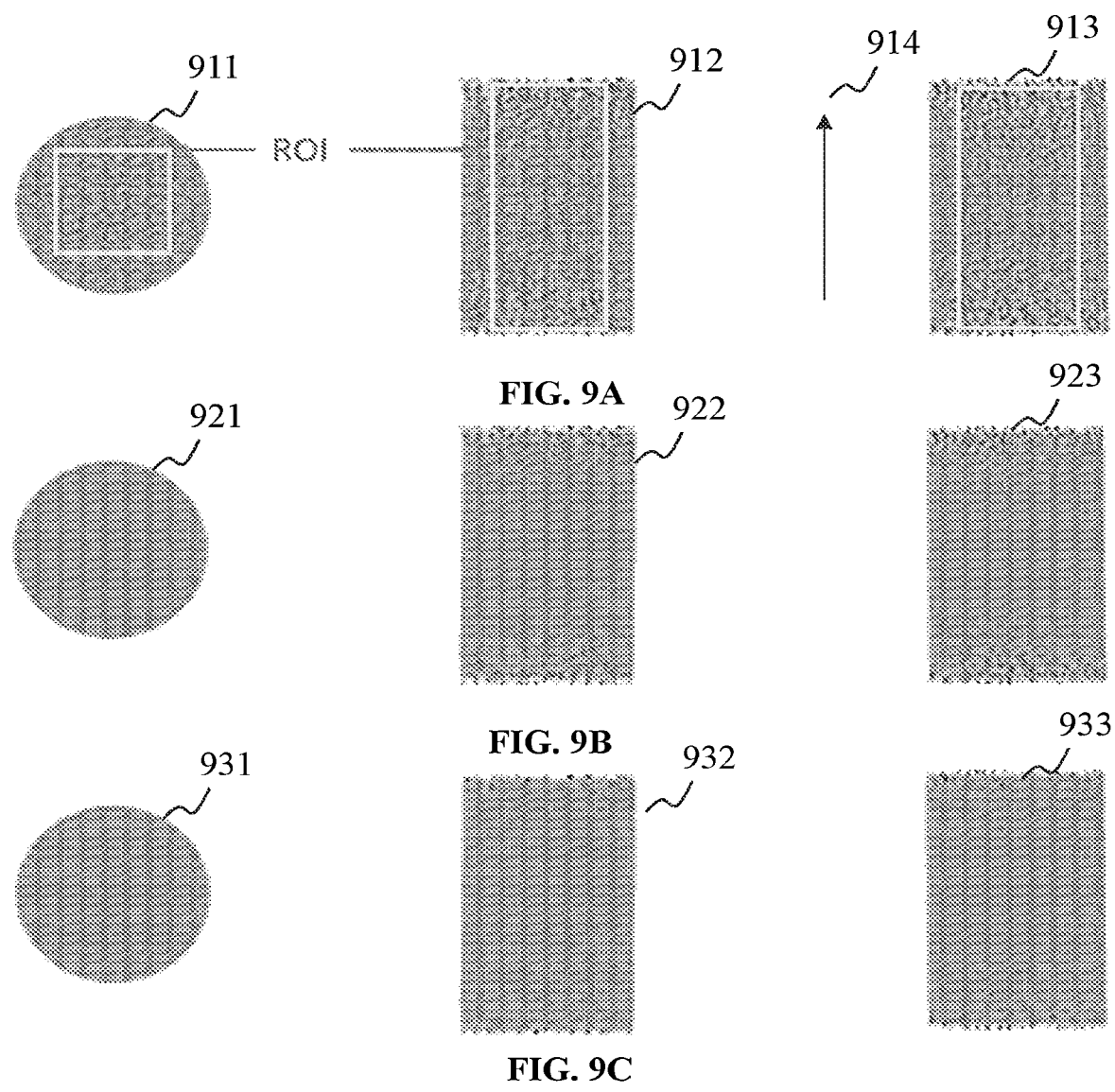

SYSTEM AND METHOD FOR MEDICAL IMAGING

CROSS-REFERENCE TO RELATED APPLICATIONS

This application is a continuation of U.S. patent application Ser. No. 16/854,838, filed on Apr. 21, 2020, which claims priority to Chinese Application No. 201910335013.7, filed on Apr. 24, 2019, the contents of each of which are hereby incorporated by reference.

TECHNICAL FIELD

The present disclosure generally relates to systems and methods for medical imaging, and more particularly, to systems and methods for noise reduction in medical images.

BACKGROUND

Medical imaging techniques including, e.g., positron emission tomography (PET), computed tomography (CT), single-photon emission computed tomography (SPECT), etc., are widely used in clinical diagnosis and/or treatment. In a medical imaging process of a subject, one or more images of the subject may be reconstructed. Noise usually appears in a reconstructed image of the subject, which may influence the quality of the image, and in turn may bring about difficulties on diagnosis performed based on the image. Thus, it is desirable for a system and method for reducing noise in medical images efficiently and conveniently.

SUMMARY

According to one aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The following operations may include obtaining a preliminary image and scanning data of a subject acquired using a scanner; determining a regularization parameter for a regularization item of an objective function based at least in part on the scanning data, wherein the regularization parameter includes at least two of a first component characterizing quality of the scanning data, a second component characterizing the scanner, or a third component characterizing a feature of the subject; and generating an image of the subject by reconstructing the preliminary image based on the objective function.

According to another aspect of the present disclosure, a method implemented on a computing device having a processor and a computer-readable storage device is provided. The method may include obtaining a preliminary image and scanning data of a subject acquired using a scanner; determining a regularization parameter for a regularization item of an objective function based at least in part on the scanning data, wherein the regularization parameter includes at least two of a first component characterizing quality of the scanning data, a second component characterizing the scanner, or a third component characterizing a feature of the subject; and generating an image of the subject by reconstructing the preliminary image based on the objective function.

In some embodiments, the scanning data is positron emission tomography (PET) data or computed tomography (CT) data.

In some embodiments, the first component relates to a noise equivalent counts.

In some embodiments, the noise equivalent counts relates to the PET data.

In some embodiments, the second component relates to a plurality of sensitivity values of a spatial sensitivity of the scanner.

In some embodiments, each of the plurality of sensitivity values relate to the PET data corresponding a point in a scanning region of the scanner.

In some embodiments, the third component relates to at least one of attenuation information or boundary information of the subject.

In some embodiments, the attenuation information is determined based on a CT image or a magnetic resonance (MR) image of the subject.

In some embodiments, the boundary information of the subject is determined based on a CT image, an MR image, or the preliminary image.

In some embodiments, the regularization parameter further includes one or more global factors that relates to at least one of the image or the subject.

In some embodiments, one of the one or more global factors includes a noise adjustment coefficient for adjusting a noise level of the image.

In some embodiments, one of the one or more global factors includes a general parameter of the subject.

In some embodiments, the objective function includes at least one of a total variation function, a quadratic function, or a Huber function.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 9A illustrates a first set of images of a phantom reconstructed based on an ordered subsets expectation maximization (OSEM) algorithm;

FIG. 9B illustrates a second set of images of a phantom reconstructed based on a regularization parameter without any component related to the spatial sensitivity of the PET scanner;

FIG. 9C illustrates a third set of images of a uniform phantom reconstructed based on a regularization parameter including a component related to the spatial sensitivity of the PET scanner;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
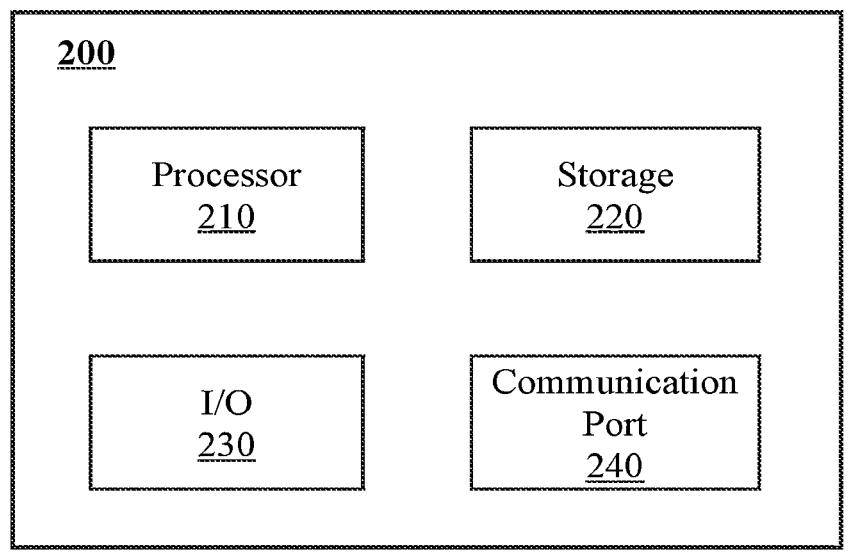
FIG. 2 is a schematic diagram illustrating hardware and/or software components of an exemplary computing apparatus according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on a computing apparatus (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and methods for image denoising in an iterative reconstruction process of an image. The image may be reconstructed based on positron emission tomography (PET) data, computed tomography (CT) data, emission computed tomography (ECT) system, etc. For illustration purposes, the disclosure describes systems and methods for radiation therapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

According to an aspect of the present disclosure, scanning data and a preliminary image of a subject is acquired. Noise in the preliminary image may correlate with at least one of a plurality of factors including, e.g., the quality of the scanning data, the characteristics of a scanning of the subject that generates the scanning data, features of the subject, etc. According to some embodiments of the present disclosure, an objective function may be determined, based on which a denoised image of the subject may be generated in an iterative reconstruction process. The objective function may include a regularization parameter for controlling an intensity of a regularization item. In some embodiments, the regularization parameter may relate to two or more factors exemplified above. In this case, the plurality of factors that may influence the noise in an image may be embodimented via a single parameter, thus improving the efficiency and feasibility of image denoising in image reconstruction.

Figure 1:
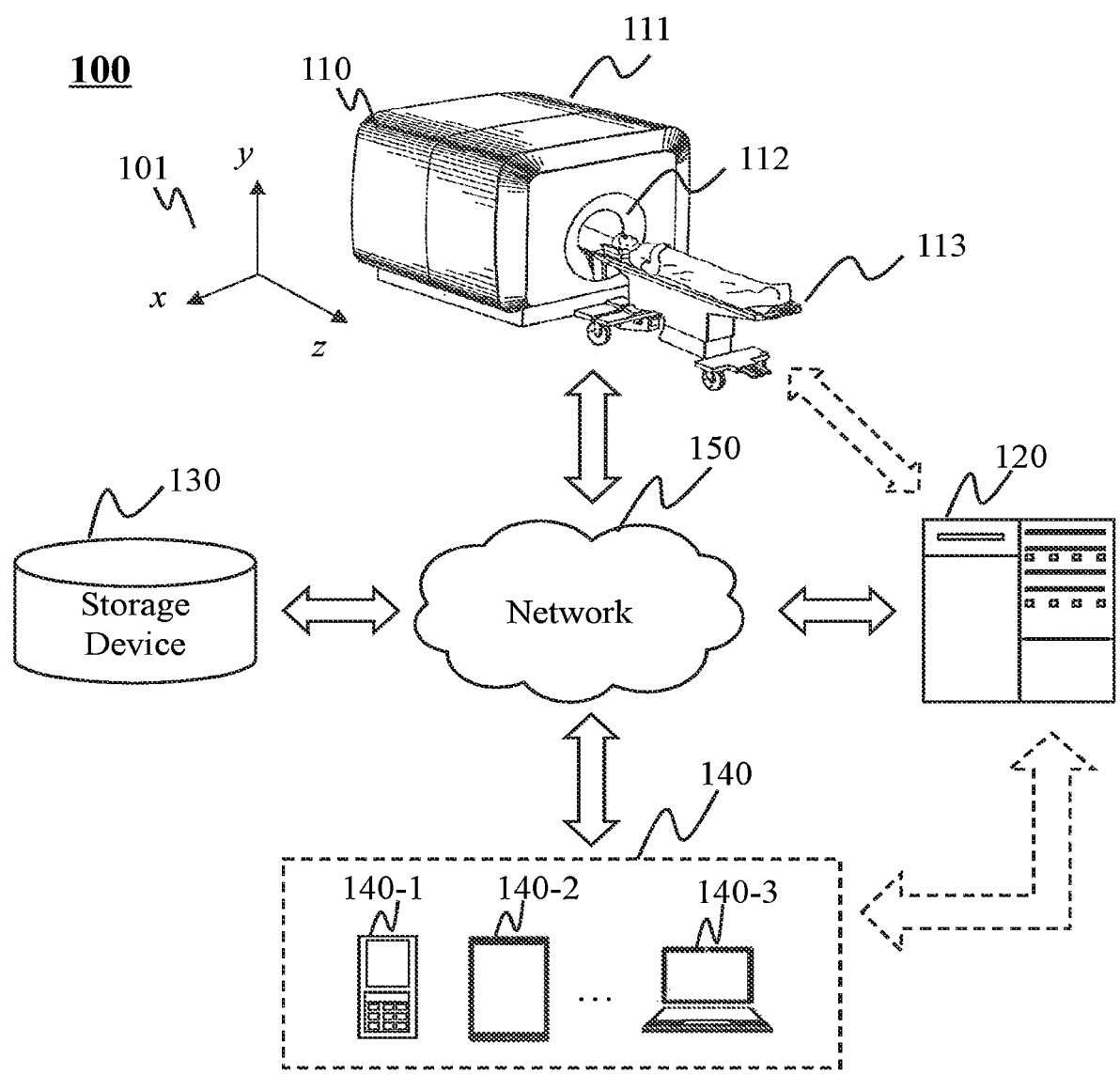
FIG. 1 is a schematic diagram illustrating an exemplary image system according to some embodiments of the present disclosure.

FIG. 1 is a schematic diagram illustrating an exemplary imaging system 100 according to some embodiments of the present disclosure. This is understood that the systems and methods for image denoising are also applicable in other systems, e.g., an industrial inspection system. The following descriptions are provided, unless otherwise stated expressly, with reference to a medical imaging system for illustration purposes and not intended to be limiting. As illustrated, the imaging system 100 may include an imaging scanner 110, a processing device 120, a storage device 130, one or more terminals 140, and a network 150. The components in the imaging system 100 may be connected in various ways. Merely by way of example, as illustrated in FIG. 1, the imaging scanner 110 may be connected to the processing device 120 through the network 150. As another example, the imaging scanner 110 may be connected with the processing device 120 directly as indicated by the bi-directional arrow in dotted lines linking the imaging scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

For illustration purposes, a coordinate system 101 including an x axis, a y-axis, and a z-axis is provided in FIG. 1. The x axis and the z axis shown in FIG. 1 may be horizontal, and the y-axis may be vertical. As illustrated, the positive x direction along the x axis may be from the right side to the left side of the imaging scanner 110 seen from the direction facing the front of the imaging scanner 110; the positive y direction along the y axis shown in FIG. 1 may be from the lower part to the upper part of the imaging scanner 110; the positive z direction along the z axis shown in FIG. 1 may refer to a direction in which the subject is moved out of the scanning channel (or referred to as the bore) of the imaging scanner 110.

The imaging scanner 110 may scan a subject or a part thereof that is located within its detection region, and generate scanning data relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof, of a patient. In some embodiments, the subject may include a specific organ, such as the heart, the esophagus, the trachea, the bronchus, the stomach, the gallbladder, the small intestine, the colon, the bladder, the ureter, the uterus, the fallopian tube, etc., or a portion thereof, of a patient. The imaging scanner 110 may include a positron emission computed tomography (PET) scanner, a computed tomography (CT) scanner, a single-photon emission computed tomography (SPECT) scanner, an emission computed tomography (ECT) scanner, or the like. In some embodiment, the imaging scanner 110 may be a multi-modality device including two or more scanners exemplified above. For example, the imaging scanner 110 may be a PET-CT scanner, a PET-MR scanner, etc.

Merely for illustration purposes, a PET-CT scanner may be provided as an example for better understanding the imaging scanner 110, which is not intended to limit the scope of the present disclosure. The PET-CT may include a gantry 111, a detecting region 112, and a bed 113. The gantry 111 may support one or more radiation sources and/or detectors (not shown). A subject may be placed on the bed 113 for CT scan and/or PET scan. The PET-CT scanner may combine a CT scanner with a PET scanner. When the imaging scanner 110 performs a CT scan, a radiation source may emit radioactive rays to the subject, and one or more detectors may detect radiation rays from the detecting region 112. The detected radiation rays may be used to generate CT data (also referred to as CT imaging information). The one or more detectors used in CT scan may include a detector (e.g., a cesium iodide detector), a gas detector, etc.

To prepare for a PET scan, a radionuclide (also referred to as "PET tracer" or "PET tracer molecules") may be introduced into the subject. The PET tracer may emit positrons in the detecting region 112 when it decays. An annihilation (also referred to as "annihilation event" or "coincidence event") may occur when a positron collides with an electron. The annihilation may produce two photons (e.g., gamma photons), which may travel in opposite directions. The line connecting the detector units that detecting the two gamma photons may be defined as a "line of response (LOR)." One or more detectors set on the gantry 111 may detect the annihilation events (e.g., gamma photons) emitted from the detecting region 112. The annihilation events emitted from the detecting region 112 may be detected and used to generate PET data (also referred to as PET imaging information). In some embodiments, the one or more detectors used in the PET scan may be different from detectors used in the CT scan. In some embodiments, the one or more detectors used in the PET scan may include crystal elements and photomultiplier tubes (PMT).

The processing device 120 may process data and/or information obtained and/or retrieve from the imaging scanner 110, the terminal(s) 140, the storage device 130 and/or other storage devices. For example, the processing device 120 may obtain scanning data from the imaging scanner 110, and reconstruct an image of the subject based on the scanning data. As another example, the processing device 120 may determine a regularization item for regularizing the image so as to reduce noise in the image and a regularization parameter for controlling an intensity of the regularization applied on the image. In some embodiments, the processing device 120 may be a single server or a server group. The server group may be centralized or distributed. In some embodiments, the processing device 120 may be local or remote. For example, the processing device 120 may access information and/or data stored in the imaging scanner 110, the terminal(s) 140, and/or the storage device 130 via the network 150. As another example, the processing device 120 may be directly connected with the imaging scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing apparatus 200 having one or more components illustrated in FIG. 2 in the present disclosure.

The storage device 130 may store data and/or instructions. In some embodiments, the storage device 130 may store data obtained from the imaging scanner 110, the terminal(s) 140, and/or the processing device 120. For example, the storage device 130 may store scanning data, signals, images, videos, algorithms, texts, instructions, program codes, etc. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the imaging system 100 (e.g., the processing device 120, the terminal(s) 140, etc.). One or more components of the imaging system 100 may access the data or instructions stored in the storage device 130 via the network 150. In some embodiments, the storage device 130 may be directly connected or communicate with one or more components of the imaging system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, a terminal 140 may be used to perform one or more tasks including, e.g., at least a portion of image reconstruction, providing user data of a user (e.g., the level of obesity of a patient, the weight of the patient, the height of the patient, the age of the patient, etc.), presentation of at least one image or relevant information, facilitating user interaction with one or more other component of the imaging system 100, etc. In some embodiments, the mobile device 140-1 may include a smart home device, a wearable device, a smart mobile device, a virtual reality device, an augmented reality device, or the like, or any combination thereof. In some embodiments, the smart home device may include a control device of an intelligent electronic apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 140 may remotely operate the imaging scanner 110. In some embodiments, the terminal(s) 140 may operate the imaging scanner 110 via a wireless connection. In some embodiments, the terminal(s) 140 may receive information and/or instructions inputted by a user, and send the received information and/or instructions to the imaging scanner 110 or the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

The network 150 may include any suitable network that can facilitate the exchange of information and/or data for the imaging system 100. In some embodiments, one or more components of the imaging system 100 (e.g., the imaging scanner 110, the terminal(s) 140, the processing device 120, or the storage device 130) may communicate information and/or data with one or more other components of the imaging system 100 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected with the network 150 to exchange data and/or information.

It should be noted that the above description of the imaging system 100 is merely provided for the purposes of illustration, not intended to limit the scope of the present disclosure. For persons having ordinary skills in the art, components contained in the imaging system 100 may be combined or adjusted in various ways, or connected with other components as sub-systems, and various variations and modifications may be conducted under the teaching of the present disclosure. However, those variations and modifications may not depart the spirit and scope of this disclosure. For example, the imaging scanner 110 may be a standalone device external to the imaging system 100, and the imaging system 100 may be connected to or in communication with the imaging scanner 110 via the network 150. All such modifications are within the protection scope of the present disclosure.

FIG. 2 is a schematic diagram illustrating hardware and/or software components of an exemplary computing apparatus 200 on which the processing device 120 may be implemented according to some embodiments of the present disclosure. As illustrated in FIG. 2, the computing apparatus 200 may include a processor 210, storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the imaging scanner 110, the terminal(s) 140, the storage device 130, and/or any other component of the imaging system 100. Specifically, the processor 210 may process scanning data obtained from the imaging scanner 110. For example, the processor 210 may generate an image based on the scanning data. In some embodiments, the image may be stored in the storage device 130, the storage 220, etc. In some embodiments, the image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing apparatus 200. However, it should be noted that the computing apparatus 200 in the present disclosure may also include multiple processors. Thus operations and/or method steps that are performed by one processor as described in the present disclosure may also be jointly or separately performed by the multiple processors. For example, if in the present disclosure the processor of the computing apparatus 200 executes both operation A and operation B, it should be understood that operation A and operation B may also be performed by two or more different processors jointly or separately in the computing apparatus 200 (e.g., a first processor executes operation A and a second processor executes operation B, or the first and second processors jointly execute operations A and B).

The storage 220 may store data/information obtained from the imaging scanner 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for reducing noise in an image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the imaging scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
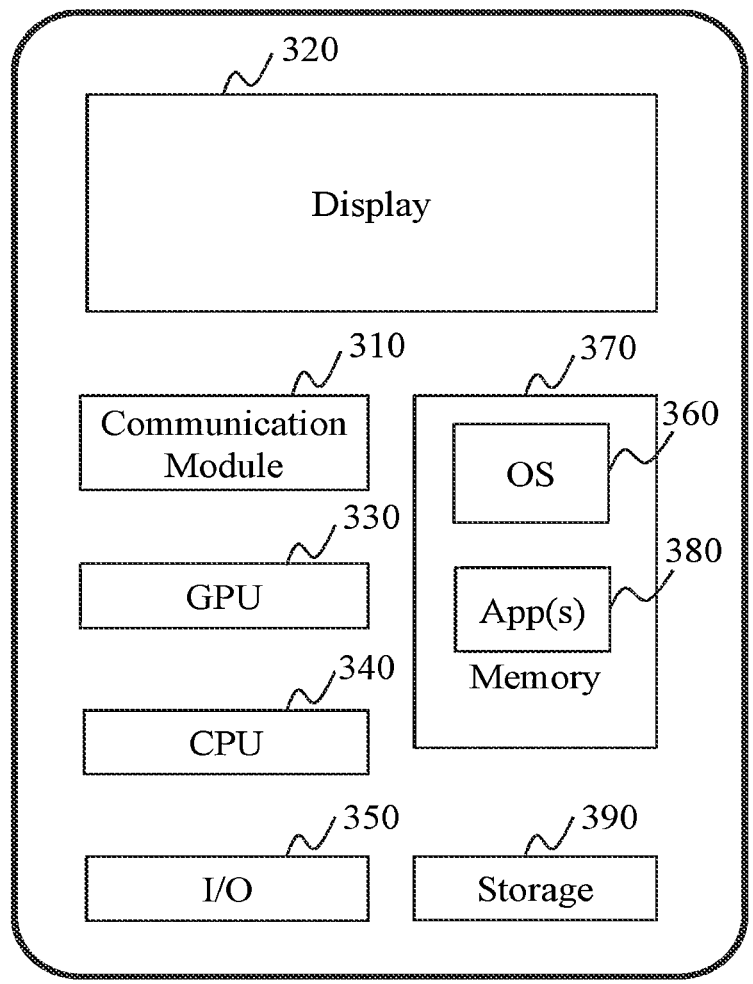
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication module 310, a display 320, a graphics processing unit (GPU) 330, a central processing unit (CPU) 340, an I/O 350, a memory 370, and storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to data processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
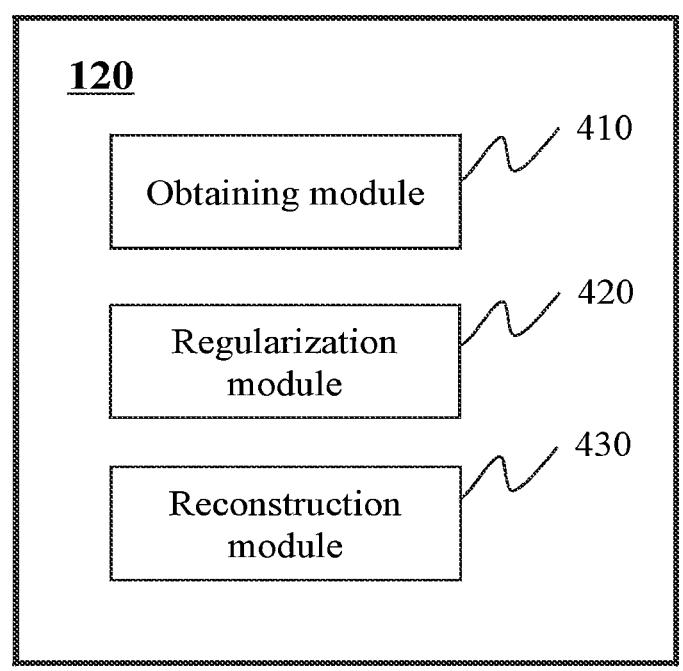
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, a regularization module 420, and a reconstruction module 430. One or more of the modules of the processing device 120 may be interconnected. The connection(s) may be wireless or wired. At least a portion of the processing device 120 may be implemented on a computing apparatus as illustrated in FIG. 2 or a mobile device as illustrated in FIG. 3.

The obtaining module 410 may data and/or information. The obtaining module 410 may obtain data and/or information from the imaging scanner 110, the processing device 120, the storage device 130, the terminal(s) 140, or any devices or components capable of storing data via the network 150. For example, the obtaining module 410 may obtain data and/or information from a medical cloud data center (not shown) via the network 150. The obtained data and/or information may include scanning data, processed results (e.g., a preliminary image, a denoised image, etc.), user instructions, algorithms, parameters (e.g., scanning parameters of the scanner 110), program codes, information of a subject, or the like, or a combination thereof. In some embodiments, the obtaining module 410 may obtain a preliminary image and scanning data of a subject. The preliminary image and the scanning data may be obtained from the imaging scanner 110, a storage device (e.g., the storage device 130, the storage 220, etc.), or any other devices or components of the imaging system 100. In some embodiments, the obtaining module 410 may transmit the obtained data and/or information to a computing device (including, for example, the regularization module 420, the reconstruction module 430, etc.) for processing.

The regularization module 420 may determine a regularization parameter for a regularization item of an objective function. In some embodiments, the regularization parameter for the regularization item of the objective function may be determined based at least in part on the scanning data. The objective function may refer to a target function to be minimized in the iterative image reconstruction process such that noise and/or artifacts in the image may be reduced or eliminated. In some embodiments, the objective function may also be referred to as a cost function. The regularization item may be an item that regularizes an image during an image reconstruction process. The regularization item may also be referred to as a penalty term. During the iterative image reconstruction process, noise in the image may be suppressed or eliminated based on the regularization item such that an overall smoothness of the image may be improved. In some embodiments, the regularization item may be provided as part of default settings of the imaging system 100. In some embodiments, the regularization item may be specified by a user according to actual needs. The regularization parameter may refer to a parameter used as a coefficient relating to the regularization item. The regularization parameter may adjust the weight of the regularization item in the objective function, thereby controlling or adjusting a strength of regularization applied on the image.

In some embodiments, the regularization parameter may include a plurality of components. In some embodiments, the plurality of components may include at least one component characterizing the quality of the scanning data (referred to as "first component" for brevity), at least one component characterizing the imaging scanner 110 (referred to as "second component" for brevity), at least one component characterizing features of the subject (referred to as "third component" for brevity), and one or more additional components. Illustratively, the imaging scanner 110 may be a PET scanner. Accordingly, the scanning data may be projection data. In this case, the first component(s) may relate to a noise equivalent counts (NEC). The second component(s) may relate to a spatial sensitivity of the PET scanner. The third component(s) may relate to attenuation information and/or boundary information of anatomical structures of the subject. The plurality of components may correspond to the one or more factors that influence the noise level and/or noise distribution in the image of the subject. The plurality of components or at least a part thereof may control the regularization of the image jointly.

The reconstruction module 430 may reconstruct an image of the subject. In some embodiments, the reconstruction module 430 may generate a denoised image of the subject by reconstructing the preliminary image based on the objective function. In some embodiments, the reconstruction module 430 may reconstruct the image in an iterative process. The iterative image reconstruction process may terminate when a threshold number or count of iterations is performed or a desired image is obtained.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules. In some embodiments, two or more units in the processing device 120 may form one module. However, those variations and modifications also fall within the scope of the present disclosure.

Figure 5:
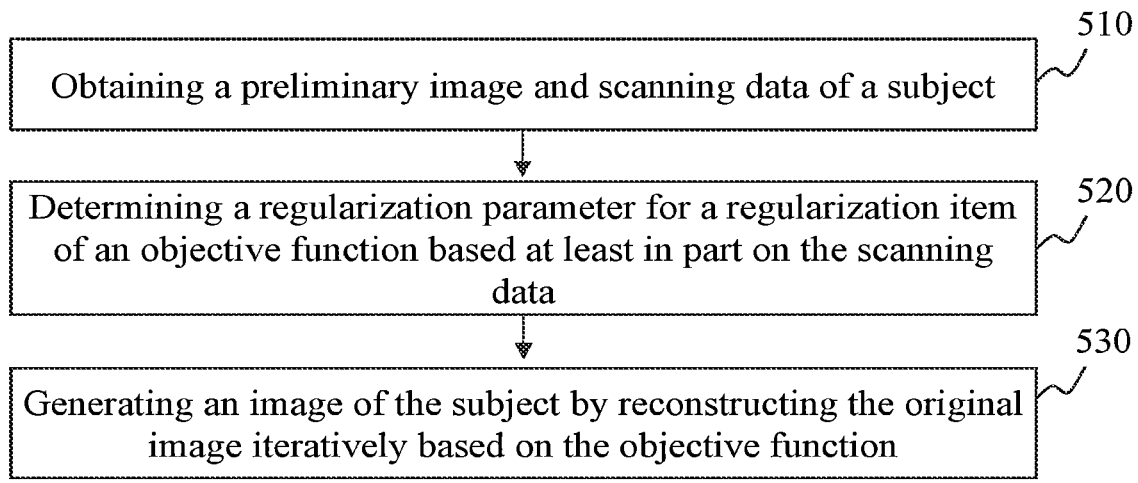
FIG. 5 includes a flowchart illustrating an exemplary process for image denoising in an image reconstruction according to some embodiments of the present disclosure.

FIG. 5 includes a flowchart illustrating an exemplary process for generating a denoised image according to some embodiments of the present disclosure. In some embodiments, at least a portion of the process 500 may be performed by the processing device 120 (e.g., implemented in the computing apparatus 200 shown in FIG. 2, the processing device illustrated in FIG. 4). In some embodiments, at least a portion of the process 500 may be performed by a terminal device (e.g., the mobile device 300 shown in FIG. 3) embodying software and/or hardware.

In 510, a preliminary image and scanning data of a subject may be obtained. In some embodiments, the preliminary image and the scanning data may be obtained by obtaining module 410.

The scanning data may be generated by the imaging scanner 110. The imaging scanner 110 may be, for example, a PET scanner, a CT scanner, an ECT scanner, a SPECT scanner, etc. Illustratively, the imaging scanner 110 may be a PET scanner. When the PET scanner scans the subject (e.g., a phantom, a patient, etc.), detectors of the PET scanner may detect annihilation events in forms of gamma phantoms from, for example, the detecting region 112. Electric signals may be generated based on the detected annihilation events through a photoelectric conversion. The PET scanner may process the electric signals, and generate PET data of the subject. The PET data may also be referred to as projection data. The PET data may be determined as the scanning data.

In some embodiments, the process 500 for generating a denoised image may be or include an iterative image reconstruction process. The preliminary image may be a first image of the subject used in the iterative reconstruction process. In some embodiments, the preliminary image may be generated by reconstructing the scanning data of the subject using a reconstruction algorithm. In this process, any suitable image reconstruction algorithms may be employed according to a type of the preliminary image (e.g., a CT image, a PET image, an ECT image, etc.). In some embodiments, the preliminary image may be any image suitable for iterative reconstruction. In some embodiments, the preliminary image may be an image stored in a storage device (e.g., the storage device 130, the storage 220, etc.) of the imaging system 100. In some embodiments, the preliminary image may be a default image applicable for any subject or a portion thereof. For example, an image of lungs of a human may be defined as a default image, which may be a general image applicable for any person. The default image may be pre-stored in the imaging system 100.

In 520, a regularization parameter for a regularization item of an objective function may be determined based at least in part on the scanning data. In some embodiments, the regularization parameter may be determined by the regularization module 420.

The objective function may refer to a target function to be minimized in the iterative image reconstruction process such that noise and/or artifacts in the image may be reduced or eliminated. It should be noted that the terms "image" and "reconstructed image" are used interchangeably in the present disclosure. Unless otherwise stated expressly, the "image" may also refer to a reconstructed image generated during the iterative image reconstruction process (e.g., an intermediate image reconstructed in an intermediate iteration of the iterative process, an ultimate image reconstructed in a last iteration of the iterative process, etc.). The iterative image reconstruction process may involve a termination condition relating to the objective function. In some embodiments, the objective function may also be referred to as a cost function.

The regularization item may be an item that regularizes an image during an image reconstruction process. The regularization item may also be referred to as a penalty term. During the iterative image reconstruction process, noise in the image may be suppressed or eliminated based on the regularization item such that an overall smoothness of the image may be improved. In some embodiments, the regularization item may be provided as part of default settings of the imaging system 100. In some embodiments, the regularization item may be specified by a user according to actual needs. Exemplary regularization items may include a total variation (TV) function, a quadratic function, a Huber function, etc.

The regularization parameter may refer to a parameter used as a coefficient relating to the regularization item. The regularization parameter may adjust the weight of the regularization item in the objective function, thereby controlling or adjusting a strength of regularization applied on the image. In some embodiments, one or more components regarding image denoising may be determined based at least in part on the scanning data. The one or more components may be associated with the quality of the scanning data, the imaging scanner 110, the subject, a radionuclide injected into the subject, or the like, or any combination thereof. In some embodiments, the regularization parameter may be determined based on the one or more components. More details regarding the regularization parameter may be described elsewhere in the present disclosure. See, for example, FIGS. 6A and 6B and the descriptions thereof.

In 530, an image of the subject may be generated by reconstructing the preliminary image based on the objective function. In some embodiments, the image (also referred to as denoised image) of the subject may be generated by the reconstruction module 430.

The objective function configured with the regularization parameter may be employed in the iterative image reconstruction process. Since the regularization applied on the image is associated with the scanning data, the noise in the image may be adaptively suppressed during the image reconstruction process, thereby improving the quality of the image.

According to the image reconstruction described with reference to the process 500, a processor (e.g., the processing device 120, the processor 210, or the obtaining module 410) may obtain the preliminary image and the scanning data of the subject acquired from a scanner. The regularization parameter of the objective function may be determined based at least in part on the scanning data. Since the scanning data is obtained under a particular condition (e.g., associated with the quality of the scanning data, the imaging scanner 110, the subject, a radionuclide injected into the subject, etc.), the regularization parameter may be adaptively configured according to the particular condition. Thus, the quality and accuracy of the reconstructed image may be improved.

In some embodiments, the objective function used in the iterative image reconstruction may be expressed as Formula (1):

$$\arg\min_f \|Mf-y\|_2 + \gamma \cdot U(f), \qquad (1)$$

where y denotes the scanning data of the subject, f denotes the reconstructed image, M denotes a system matrix, $\|Mf-y\|_2$ denotes a 2-norm of $Mf-y$, y denotes the regularization parameter, and U (f) denotes the regularization item. Merely by way of example, the regularization item may be a TV function.

In some embodiments, the objective function may be minimized in the iterative image reconstruction process such that noise and/or artifacts in the image may be reduced or eliminated. In some embodiment, the objective function may be divided into two parts including part (a) and part (b) as expressed in Formulae (2) and (3):

$$(a) \arg \min_f \|Mf - y\|_2, \tag{2}$$

$$(b) \arg \min_f \|f\|_{TV} + \|f^{(n)} - f\|_2, \tag{3}$$

wherein $f^{(n)}$ denotes an image reconstructed in an n-th iteration. The part (a) in Formula (2) may be a data fidelity part, and the part (b) in Formula (3) may be a regularization part for image regularization. The two parts may be minimized during the iterative image reconstruction process. In some embodiments, the iterative image reconstruction process may terminate when a threshold number or count of iterations is performed or a desired result of the first part and/or the second part (e.g., an expected image) is obtained.

In some embodiments, the solution of the part (a) may be determined through an iterative algorithm, such as an ordered subsets expectation maximization (OSEM) algorithm. The solution of the part (a) may be expressed as Formula (4):

$$f_j^{(n)} = \frac{f_j^{(n-1)}}{\sum_{i_k \in S_k} M_{i_k j}} \sum_{k \in S} M_{i_k j} \left( \frac{y_{i_k}}{\sum_{j_p \in L_{i_k}} M_{i_k j_p} f_t^{(n-1)}} \right), \tag{4}$$

where $S_k$ denotes a k-th subset of the projection data of the subject, $L_{i_k}$ denotes an $i_k$-th LOR in the k-th subset, $M_{i,j}$ may be a weight characterizing contribution of a j-th pixel in the image to the $L_{i_k}$ LOR which traverses the j-th pixel, and $f_j^{(n)}$ may be a value of the j-th pixel in an n-th iteration.

In some embodiments, the solution of the part (b) may be determined through a gradient related algorithm, such as a gradient descent algorithm. In some embodiments, the determination of the solution of the part (b) may be implemented in another iterative process. For example, the solution of the part (b) may be expressed as Formula (5):

$$f^{(n,r+1)} = f^{(n,r)} - \lambda \frac{\partial \|f\|_{TV}}{\partial f_{x,y,z}}, \tag{5}$$

where $\lambda$ denotes a step size of the gradient descent algorithm, r denotes an r-th iteration of the iterative process for determining the resolution of the part (b), and x, y, z denote three axes constituting a coordinate system, for example, the coordinate system 101 as illustrated in FIG. 1. A direction with the largest gradient descent, among the x, y, and z directions, may be determined in the coordinate system according to the gradient descent algorithm. The total variation may be expressed as Formula (6):

$$\|f\|_{TV} = \int_u |\nabla f| dx dy, \tag{6}$$

where u denotes an image or a portion thereof that needs to be reconstructed.

In some embodiments, the Formula (6) may also be expressed in a discrete form according to Formula (7):

$$\|f\|_{TV} = \sum_{x,y,z} \sqrt{\left(\frac{\partial f_{x-1,y,z}}{\partial x}\right)^2 + \left(\frac{\partial f_{x,y-1,z}}{\partial y}\right)^2 + \left(\frac{\partial f_{x,y,z-1}}{\partial z}\right)^2}. \tag{7}$$

In some embodiments, an approximate derivative of the total variation may be determined according to Formulae (8)-(12):

$$\frac{\partial \|f\|_{TV}}{\partial f_{x,y,z}} \approx G \cdot \left(\frac{\partial f_{x-1,y,z}}{\partial x} + \frac{\partial f_{x,y-1,z}}{\partial y} + \frac{\partial f_{x,y,z-1}}{\partial z}\right) - G_x \cdot \frac{\partial f_{x,y,z}}{\partial x} - G_y \cdot \frac{\partial f_{x,y,z}}{\partial y} - G_z \cdot \frac{\partial f_{x,y,z}}{\partial z}, \tag{8}$$

$$G = \left[\varepsilon + \left(\frac{\partial f_{x-1,y,z}}{\partial x}\right)^2 + \left(\frac{\partial f_{x,y-1,z}}{\partial y}\right)^2 + \left(\frac{\partial f_{x,y,z-1}}{\partial z}\right)^2\right]^{-\frac{1}{2}}, \tag{9}$$

$$G_x = \left[\varepsilon + \left(\frac{\partial f_{x,y,z}}{\partial x}\right)^2 + \left(\frac{\partial f_{x+1,y-1,z}}{\partial y}\right)^2 + \left(\frac{\partial f_{x+1,y,z-1}}{\partial z}\right)^2\right]^{-\frac{1}{2}}, \tag{10}$$

$$G_y = \left[\varepsilon + \left(\frac{\partial f_{x,y,z}}{\partial y}\right)^2 + \left(\frac{\partial f_{x-1,y+1,z}}{\partial x}\right)^2 + \left(\frac{\partial f_{x,y+1,z-1}}{\partial z}\right)^2\right]^{-\frac{1}{2}}, \tag{11}$$

$$G_z = \left[\varepsilon + \left(\frac{\partial f_{x,y,z}}{\partial z}\right)^2 + \left(\frac{\partial f_{x-1,y,z+1}}{\partial x}\right)^2 + \left(\frac{\partial f_{x,y-1,z+1}}{\partial z}\right)^2\right]^{-\frac{1}{2}}. \tag{12}$$

In this way, the solution of the part (b) may be expressed as Formula (13):

$$f^{(n,r+1)} \approx f^{(n,r)} - \lambda f_{x,y,z}(3G + G_x + G_y + G_z) + \lambda \cdot G(f_{x-1,y,z} + f_{x,y-1,z} + f_{x,y,z-1}) + \lambda \cdot (G_x f_{x+1,y,z} + G_y f_{x,y+1,z} + G_z f_{x,y,z+1}) \tag{13}$$

In some embodiments, in order to avoid a negative value of the solution of the part (b), the step size $\lambda$ may be specified as Formula (14):

$$\lambda = \frac{1}{3G + G_x + G_y + G_z}. \tag{14}$$

The $\lambda$ expressed in Formula (14) may be incorporated in the Formula (13). Then the solution of the part (b) may be expressed as Formula (15):

$$f^{(n,r+1)} = \lambda \cdot G(f_{x-1,y,z} + f_{x,y-1,z} + f_{x,y,z-1}) + \lambda \cdot (G_x f_{x+1,y,z} + G_y f_{x,y+1,z} + G_z f_{x,y,z+1}). \tag{15}$$

Thus, the solution of the part (b) may be determined as Formula (16):

$$f^{(n,r+1)} = \frac{f^{(n,r)} + \beta \cdot G(f_{x-1,y,z} + f_{x,y-1,z} + f_{x,y,z-1} + G_x f_{x+1,y,z} + G_y f_{x,y+1,z} + G_z f_{x,y,z+1})}{1 + \beta(3G + G_x + G_y + G_z)}. \tag{16}$$

In this case, the parameter γ may be replaced by the parameter β, and the regularization strength may be adjusted through the single parameter β, which may be defined as the regularization parameter.

A noise level and/or noise distribution of the image of the subject may be influenced by one or more factors. The one or more factors may include quality of the scanning data, a hardware and/or software configurations, scanning parameters, etc. of the imaging scanner 110, one or more features of the subject (e.g., attenuation information, boundary information of anatomical structures, the level of obesity of the subject, the age of the subject, the weight of the subject, etc.), a scanning condition (e.g., a dose of the radionuclide administered to the subject), etc. A noise level and/or noise distribution in the image may be different if at least one of the one or more factors changes. Merely by way of example, a distribution of noise in a reconstructed image may vary if the subject and/or a working condition of the imaging scanner 110 changes.

Conventionally, each of the one or more factors may correspond to a regularization item and a regularization parameter that serves as a weight of the regularization item. Noise introduced by a particular factor may be suppressed or eliminated by specifying a regularization item and a regularization parameter corresponding to the particular factor in the objective function. According to some embodiments of the present disclosure, a regularization item and a regularization parameter may be determined. In some embodiment, the regularization item may be specified, for example, by a user, according to default settings of the imaging system 100, etc. In some embodiments, the regularization item may be selected from the TV function, the quadratic function, the Huber function, etc. In some embodiments, the regularization item may be any suitable function that regularizes an image during an image reconstruction process. The regularization parameter may be determined by considering at least two of the one or more factors that influence the noise level and/or noise distribution in the image. In this case, noise introduced into the image by two or more factors may be suppressed or eliminated through a single parameter.

In some embodiments, the regularization parameter may include a plurality of components. In some embodiments, the plurality of components may include at least one component characterizing the quality of the scanning data (referred to as "first component" for brevity), at least one component characterizing the imaging scanner 110 (referred to as "second component" for brevity), at least one component characterizing features of the subject (referred to as "third component" for brevity), and one or more additional components. Illustratively, the imaging scanner 110 may be a PET scanner. Accordingly, the scanning data may be projection data. In this case, the first component(s) may relate to a noise equivalent counts (NEC). The second component(s) may relate to a spatial sensitivity of the PET scanner. The third component(s) may relate to attenuation information and/or boundary information of anatomical structures of the subject. The plurality of components may correspond to the one or more factors that influence the noise level and/or noise distribution in the image of the subject. The plurality of components or at least a part thereof may control the regularization of the image jointly.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 6:
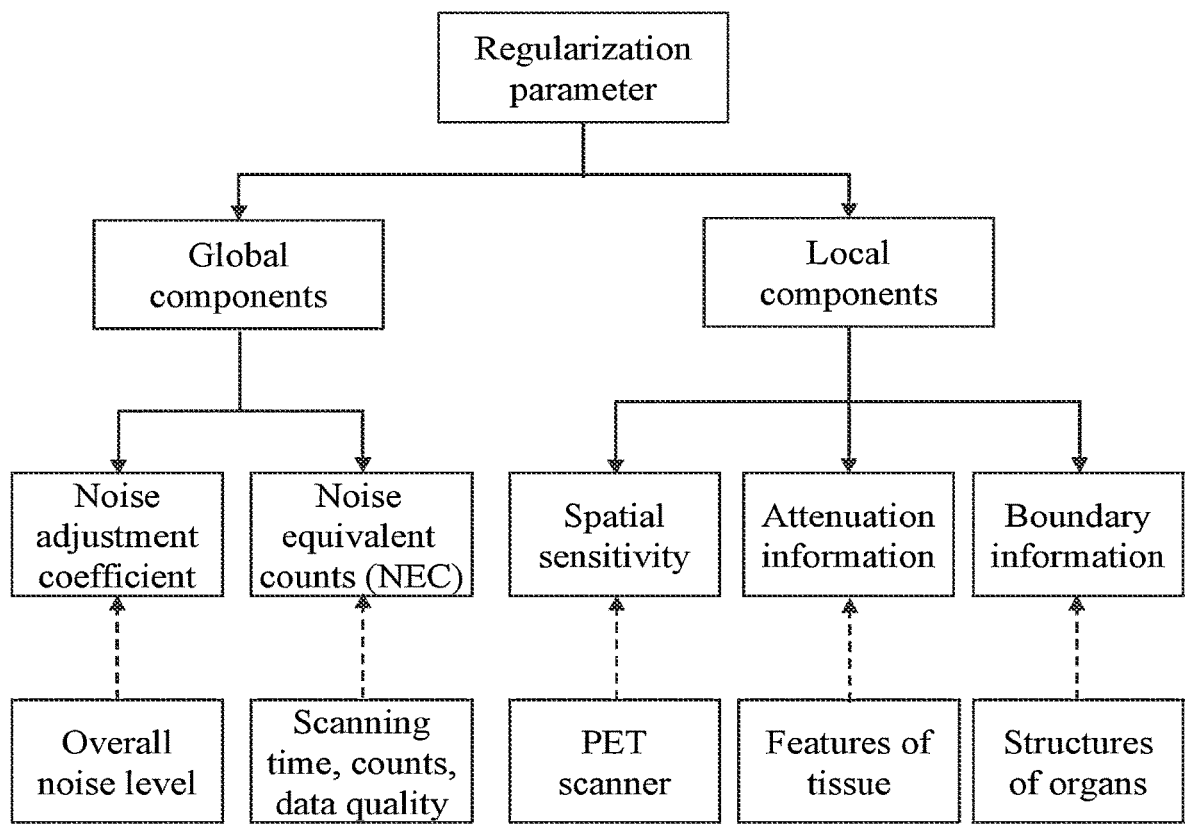
FIG. 6 is a schematic diagram of a regularization parameter including a plurality of components according to some embodiments of the present disclosure.

FIG. 6 is a schematic diagram of a regularization parameter including a plurality of components according to some embodiments of the present disclosure. The following descriptions regarding the regularization parameter are provided as exemplary embodiments in which the imaging scanner 110 is a PET scanner and the scanning data is projection data, which is merely for illustration purposes and not intended to be limiting.

As illustrated in FIG. 6, the regularization parameter may include one or more global components and one or more local components. The one or more global components may relate to the entire image of the subject uniformly. In some embodiments, the global components may include at least one constant applied over the entire image (i.e., all the pixels of the image). The at least one constant may vary for different images For example, the at least one constant may vary for images of a same subject reconstructed based on scanning data of different quality, images of different subjects, etc. The global components may control the strength of the regularization over an entire image.

The local components may be applied on a portion of the image (e.g., one or more pixels, a spatially localized region, etc.). In some embodiments, a local component may be a function of pixels (or voxels) in the image. For instance, the local component includes values each of which is for one pixel (or voxel) of the image. In some embodiments, a local component may be a function of regions in the image. For instance, the local component includes values each of which is for a region including one or more pixels (or voxels) of the image. A region of an image may include one or more pixels (or voxels) of the image that satisfy a criterion. Exemplary criteria may include that the pixel/voxel value exceeds or is below a threshold, that the change of pixel/voxel value exceeds or is below a threshold, that pixels (or voxels) are located within a specific portion of the image, or the like, or a combination thereof.

In some embodiments, the one or more global components may include a noise adjustment coefficient and the at least one first component related to a noise equivalent counts (NEC). The noise adjustment coefficient may server as a scale factor of other components (e.g., a combination of the at least one first component, the at least one second component, and the at least one third component) of the regularization parameter. The noise adjustment coefficient may adjust the magnitude of the regularization parameter, and control a strength of the regularization applied to the entire image. In this way, an overall noise level of the image may be adjusted through the noise adjustment coefficient.

The NEC may relate to the quality of the PET data of the subject, a scanning time of a PET scan on the subject, counts of coincidence events detected during the PET scan, etc. The NEC may be an accumulation of noise equivalent count rates (NECR) over a period of time. The NECR may represent equivalent count rates of true coincidence events of images with a same signal-to-noise ratio (SNR) on the condition that the PET scanner is in an ideal state. As used herein, the ideal state refers to a hypothetical state in which no error or imperfection present in the PET scanner and its operation. A total count of true coincidence events (equivalent to the NEC) may be more precise in representing the quality of the projection data than the count rates of true coincidence events (equivalent to the NECR). The image reconstruction based on projection data of different quality may affect the quality of the reconstructed image directly.

In some embodiments, the one or more local parameters may include the at least one second component related to a spatial sensitivity of the PET scanner and the at least one third component related to attenuation information and/or boundary information of anatomical structures of the subject. The spatial sensitivity of the PET scanner may be represented by a plurality of sensitivity values. Each of the plurality of sensitivity values may correspond to a point (e.g., simplified as a unit volume or a voxel) in the scanning region of the PET scanner. In some embodiments, the scanning region of the PET scanner may be the detecting region 112 or a portion thereof.

Detectors of the PET scanner may be set around the subject. Since different detectors have different efficiency in detecting annihilation events (e.g., gamma photons) from the scanning region of the PET scanner, the sensitivity values at different points in the scanning region may be different. For example, the PET scanner may have a cylinder-shaped scanning region. A sensitivity value at a central point of the scanning region of the PET scanner may be higher than a sensitivity value at an end point in an axial direction of the cylinder-shaped scanning region. The spatial sensitivity of the PET scanner may affect the distribution of noise in an image reconstructed based on data acquired by the PET scanner.

The attenuation information of the subject may relate to features including, for example, a size, a shape, a density, etc. of tissue of the subject. In some embodiments, the attenuation information of the subject may be embodied in photons (e.g., gamma photons) traverse internal structures of the subject. Photons emitted from a source may have different attenuation values when the photons traverse different media (e.g., tissue of different types in the body of the subject). The larger an attenuation coefficient corresponding to a medium and/or a distance that the gamma photon passes through in the medium is, the greater the energy loss of the gamma photon may be. Generally, a larger energy loss of the gamma photon may result in relatively larger errors in the projection data. Errors of the projection data with different magnitudes may bring about different noise levels in the image.

The boundary information of the subject may relate to anatomical structures of organs of the subject. During the image denoising process, sharpness of the boundaries of structures in the image may be maintained or improved. Boundaries of structures in the image may be effectively utilized in identifying regions of boundaries, regions of background, regions of a specific tissue, regions of specific organs, etc., thereby improving the accuracy of the reconstructed image. By extracting the boundaries of structures in the image, regularization of different strengths may be applied to different regions.

In some embodiments, the regularization parameter may be determined according to the Formula (17):

$$\beta = a \cdot g(\text{NEC}) \cdot \varphi(\text{sensitivity}) \cdot \phi(\text{attenuation}) \cdot \psi(\text{boundary}), \quad (17)$$

where $\beta$ denotes the regularization parameter, $a$ denotes the noise adjustment coefficient, $g(\text{NEC})$ denotes a first component related to the NEC, $\varphi(\text{sensitivity})$ denotes a second component related to the spatial sensitivity of the PET scanner, $\phi(\text{attenuation})$ denotes a third component related to attenuation information of the subject, and $\Psi$ (boundary) denotes another third component related to boundary information of structures of the subject.

Each of the one or more factors or a part thereof that influence the noise in the image may be characterized by one of the above components through a particular function or algorithm. The particular function or algorithm may represent a relationship between each of the one or more factors or a part thereof and the noise in the image. Various ways may be used to adjust the components. In some embodiments, it may be assumed that the regularization intensity is proportional to a variation of the noise.

In some embodiments, the noise adjustment coefficient may be a constant or a variable. For example, the noise adjustment coefficient may be 0.1, 0.2, 0.5, 2, 5, etc. In some embodiments, the noise adjustment coefficient may be set by a user (e.g., a doctor, a technician, etc.), according to default settings of the imaging system 100, etc. For example, the noise adjustment coefficient may be an empirical-based number specified by a user.

In some embodiments, the NEC may be obtained by processing the scanning data (i.e., projection data in a case that the imaging scanner 110 is a PET scanner). In some embodiments, the NEC may have a correlation with the SNR of the image.

Figure 7:
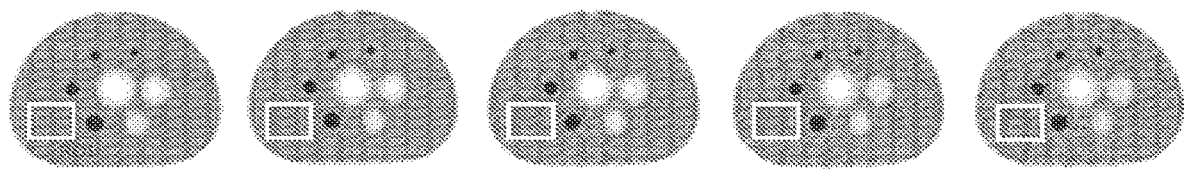
FIG. 7 illustrates five images of a subject reconstructed based on a constant regularization parameter under different NEC values according to some embodiments of the present disclosure.

An example regarding the relationship between the NEC and the noise in the image is provided for illustration purposes. FIG. 7 illustrates five images of a subject reconstructed based on a constant regularization parameter under different NEC values according to some embodiments of the present disclosure. The NEC of the five reconstructed images decrease gradually from left to right. The NEC of the five reconstructed images are $1.34e^8$, $6.73e^7$, $3.38e^7$, $1.66e^7$, $8.5e^6$, respectively. A rectangle box in solid lines of a white color denotes a region of interest in each of the five reconstructed images. As illustrated in FIG. 7, the noise level in the ROIs increases from left to right gradually.

Figure 8A:
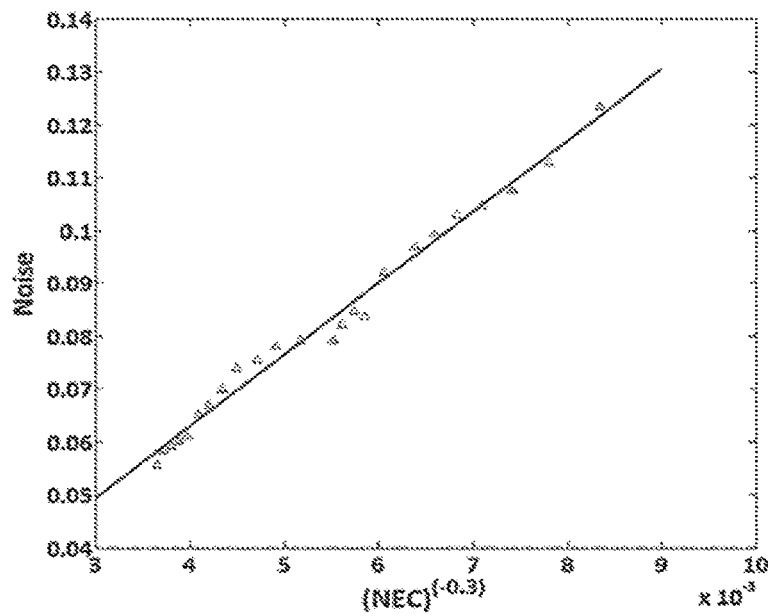
FIG. 8A illustrates a relationship between NEC and noise in twenty images of a subject reconstructed based on a constant regularization parameter according to some embodiments of the present disclosure.

FIG. 8A illustrates a relationship between NEC and noise in twenty images of a subject reconstructed based on a constant regularization parameter according to some embodiments of the present disclosure. Each triangle represents one of the twenty reconstructed images. As shown in FIG. 8A, values of noise and the NEC may follow a linear distribution. A representation (e.g., a value) of noise in an image may be proportional to the value of the NEC if the image is reconstructed based on a constant regularization parameter.

Figure 8B:
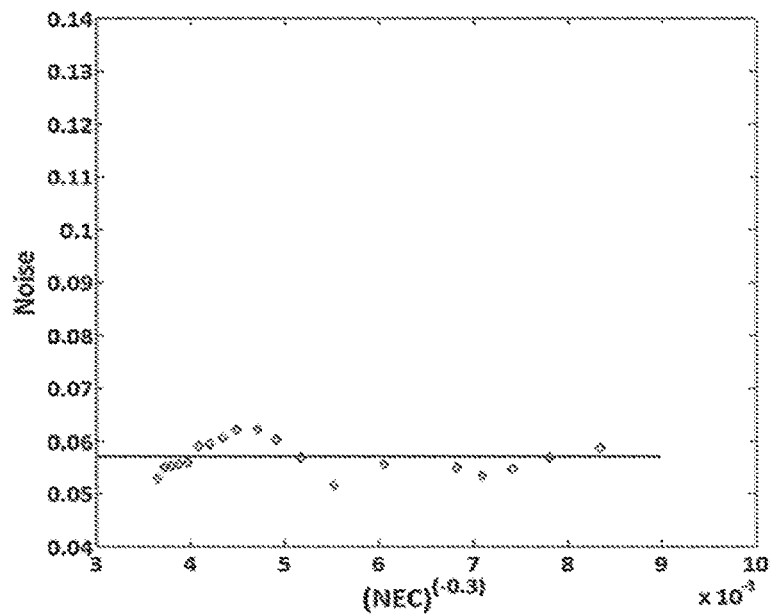
FIG. 8B illustrates a relationship between NEC and noise in twenty images of the subject reconstructed based on a regularization parameter including a component related to the NEC according to some embodiments of the present disclosure.

FIG. 8B illustrates a relationship between NEC and noise in other twenty images of the subject (the same subject as that whose images are shown in FIG. 8A) reconstructed based on a regularization parameter including a component related to the NEC according to some embodiments of the present disclosure. Each quadrangle may represent one of the other twenty reconstructed images. In comparison with FIG. 8A, the value of noise in an image may be substantially constant if the image is reconstructed based on a regularization parameter (e.g., the regularization parameter in Formula (21)) including a component related to the NEC. Thus, noise introduced into an image due to the NEC, which may represent the quality of the projection data, may be effectively suppressed if the image is reconstructed based on a regularization parameter including a component related to the NEC.

In some embodiments, the value of the noise in the image may be expressed as Formula (18):

$$\text{Noise} = \sqrt{\frac{1}{n-1} \sum_{i=1}^{t} \left(\frac{f_i}{\bar{f}} - 1\right)^2}, \quad (18)$$

where t denotes the number or count of pixels in a region of interest (ROI) in the image, $f_i$ denotes the value of an i-th pixel in the ROI, and $\bar{f}$ denotes an average value of pixels in the ROI.

In some embodiments, the relationship between the value of noise and the NEC may be provided according to Formula (19):

$$\text{Noise} = 13.52 \cdot (NEC)^{(-0.3)} + 0.008846, \qquad (19)$$

where the coefficient 13.52, the negative exponent −0.3, and the constant 0.008846 are derived based on a plurality of sample images of a subject (e.g., the images in FIGS. 8A and 8B). In some embodiments, these three values may vary in a small scale (e.g., less than 5%, 10%, or 20%) for different patients or different regions (e.g., different organs, tissue) of a same subject or different subjects.

In some embodiments, it may be inferred that:

$$g(NEC) \propto (NEC)^{(-0.3)}. \qquad (20)$$

In some embodiments, the regularization parameter may be determined according to Formula (21) considering the noise adjustment coefficient and the NEC:

$$\beta = a \cdot (NEC)^{(-0.3)}. \qquad (21)$$

In some embodiments, the spatial sensitivity of the PET scanner may be obtained based on the projection data. In some embodiments, since a distribution of photons emitted from the subject may conform to a Poisson distribution, a variance of each photon corresponding to different spatial sensitivity values may be estimated. Merely for illustration purposes, two arbitrary photons sources (i.e., points) A and B in the scanning region of the PET scanner are defined. Activities of the two sources may be $\lambda_A$ and $\lambda_B$. Spatial sensitivity values of the two sources may be $S_A$ and $S_B$. Expected values of the activities of the two sources may be determined according to Formulae (22) and (23):

$$E(A) = \lambda_A, \qquad (22)$$

$$E(B) = \lambda_B. \qquad (23)$$

The expected values of the activities of the two sources may equal to variance values of the activities of the two sources, respectively. The variance values of the activities of two gamma photons emitted in a unit time may be determined according to Formulae (24) and (25):

$$D(S_A \cdot A) = E(S_A \cdot A) = S_A \cdot \lambda_A, \qquad (24)$$

$$D(S_B \cdot B) = E(S_B \cdot B) = S_B \cdot \lambda_B. \qquad (25)$$

According to the definition of noise in Formula (18), it may be inferred that:

$$\text{Noise}(A) = \frac{\sqrt{D(A)}}{\lambda_A} = \frac{1}{\sqrt{S_A \cdot \lambda_A}}, \qquad (26)$$

$$\text{Noise}(B) = \frac{\sqrt{D(B)}}{\lambda_B} = \frac{1}{\sqrt{S_B \cdot \lambda_B}}. \qquad (27)$$

As for the two sources in the scanning region of the PET scanner, a relationship between the noise at the two sources may be determined according to Formula (28):

$$\frac{N(A)}{N(B)} = \frac{\sqrt{S_B \cdot \lambda_B}}{\sqrt{S_A \cdot \lambda_A}}, \qquad (28)$$

where N(A) may be a simplified expression of Noise(A), and N(B) may be a simplified expression of Noise(B). The noise distribution and the spatial sensitivity of the PET scanner may have a relationship expressed as:

$$N \propto \frac{1}{\sqrt{S \cdot \lambda}}. \qquad (29)$$

In a specific applications, the activity of a source may be omitted in the relationship expressed as Formula (29). Thus, the second component related to the spatial sensitivity of the PET scanner may be:

$$\phi(\text{sensitivity}) \propto \frac{1}{\sqrt{S}}. \qquad (30)$$

In some embodiments, the regularization parameter may be determined according to Formula (31) considering the noise adjustment coefficient, the NEC, and the spatial sensitivity of the PET scanner:

$$\beta_j = a \cdot (NEC)^{(-0.3)} \cdot \frac{1}{\sqrt{S_j}}, \qquad (31)$$

where $\beta_j$ denotes the regularization parameter at a j-th point in the image, and $S_j$ denotes a sensitivity value at a corresponding j-th point in the scanning region of the PET scanner.

To better illustrate the effect of the regularization parameter including a component related to the spatial sensitivity of the PET scanner, a phantom made of a uniform material may be scanned by the PET scanner. In the following example, the phantom may be a cylindrical phantom.

FIG. 9A illustrates a first set of images of a phantom reconstructed based on an ordered subsets expectation maximization (OSEM) algorithm. The OSEM algorithm may also be an iterative algorithm. The first set of images of the phantom may include a cross-sectional image 911, a coronal image 912, and a sagittal image 913. A cylindrical ROI may be specified in the phantom (e.g., as illustrated by a rectangle box in white solid lines in each of the first set of images). As illustrated in FIG. 9A, a relatively high noise level appears as background noise in the ROI.

FIG. 9B illustrates a second set of images of a phantom reconstructed based on a regularization parameter without any component related to the spatial sensitivity of the PET scanner. The second set of images of the phantom may include a cross-sectional image 921, a coronal image 922, and a sagittal image 923. An ROI of a same shape and position as the ROI in FIG. 9A may be defined in the phantom (not shown in the figure). As illustrated in FIG. 9B, in a length direction (i.e., the direction 914 as illustrated in FIG. 9A) of the phantom, a middle part of the ROI may have a relatively low noise level and an end part of the ROI may have a higher noise level.

FIG. 9C illustrates a third set of images of a uniform phantom reconstructed based on a regularization parameter including a component related to the spatial sensitivity of the PET scanner. The third set of images of the phantom may include a cross-sectional image 931, a coronal image 932, and a sagittal image 933. An ROI of a same shape and position as the ROIs in FIGS. 9A and 9B may be defined in the phantom (not shown in the figure). As illustrated in FIG. 9C, the noise level in the ROI is substantially uniform and relatively low compared to the noise level in the ROI of FIG. 9A.

In some embodiments, a plurality of layers may be determined in the length direction of the uniform phantom. The number or count of the plurality of layers may be set by a user, according to default settings of the imaging system 100, etc. Values of noise in images of the plurality of layers reconstructed based on the OSEM algorithm, the regularization parameter without any component related to the spatial sensitivity of the PET scanner, and/or the regularization parameter including a component related to the spatial sensitivity of the PET scanner, respectively may be quantitatively analyzed.

Figure 9D:
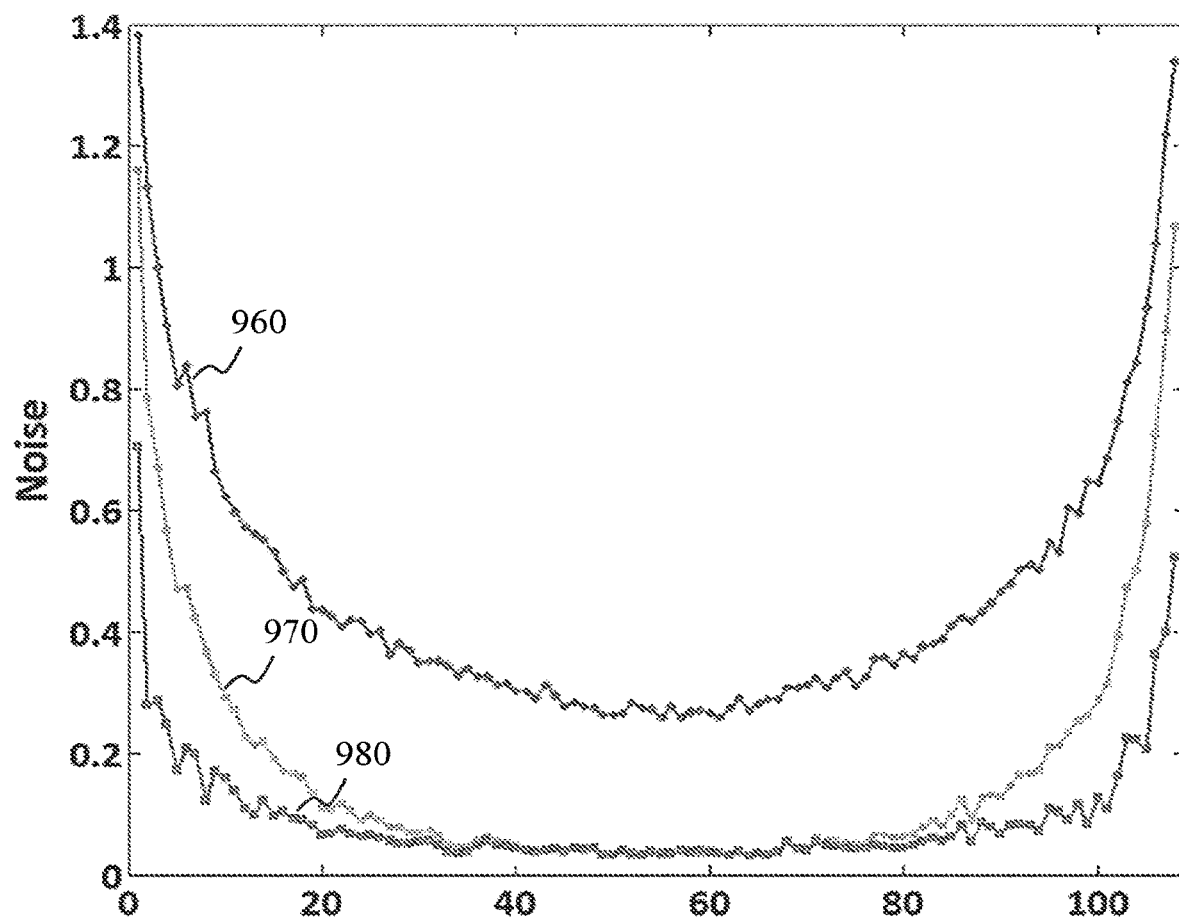
FIG. 9D illustrates a schematic diagram of noise variance curves corresponding to different reconstruction algorithms according to some embodiments of the present disclosure.

FIG. 9D illustrates a schematic diagram of noise variance curves corresponding to different reconstruction algorithms according to some embodiments of the present disclosure. A noise variance curve may indicate the variation of noise among images of different layers reconstructed based on a particular algorithm. A horizontal axis of the noise variance curve may be a sequence of layers in the length direction of the phantom. A vertical axis of the noise variance curve may be the value of noise. As illustrated in FIG. 9D, a first curve 960 is a noise variance curve corresponding to the OSEM algorithm, a second curve 970 is a noise variance curve corresponding to the regularization parameter without any component related to the spatial sensitivity of the PET scanner, and a third curve 980 is a noise variance curve corresponding to the regularization parameter including a component related to the spatial sensitivity of the PET scanner. The regularization parameter including the component related to the spatial sensitivity of the PET scanner (i.e., corresponding to the third curve 980) may effectively suppress the noise in the reconstructed image.

In some embodiments, the attenuation information of the subject may be determined based on one or more images that may be used to distinguish tissue of different types and/or structures of the subject. In some embodiments, the one or more images may include a CT image, a magnetic resonance (MR) image, etc. In some embodiments, the CT image may be generated by performing a CT scan on the subject using a CT scanner. In some embodiments, the MR image may be generated by performing an MR scan on the subject using an MR scanner. The CT scan and/or the MR scan may be performed before, after, or in parallel with the PET scan that generates the projection data.

In some embodiments, the attenuation information may be represented by an attenuation factor in a certain direction. The attenuation factor in the direction may be determined according to Formula (32):

$$ACE = e^{\int -\mu l dl}, \quad (32)$$

where ACE denotes the attenuation factor in the certain direction, $\mu$ denotes a linear attenuation coefficient of tissue in the direction, and l denotes a thickness of the tissue in the direction.

The attenuation information may be represented or calculated through chordal graphs. In some embodiments, the attenuation information may be combined with the spatial sensitivity of the PET scanner for simplicity. In some embodiments, the calculation of the attenuation information may be incorporated into the process in which the spatial sensitivity of the PET scanner is determined. For example, a spatial sensitivity map containing attenuation information of the subject, which includes both the spatial sensitivity of the PET scanner and the attenuation information of the subject, may be determined.

In some embodiments, the regularization parameter may be determined according to Formula (33) considering the noise adjustment coefficient, the NEC, the spatial sensitivity of the PET scanner, and the attenuation information of the subject:

$$\beta_j = a \cdot (NEC)^{(-0.3)} \cdot \frac{1}{\sqrt{\text{sns\_map}_j}}, \quad (33)$$

where $\beta_j$ denotes the regularization parameter at the j-th point in the image, and $\text{sns\_map}_j$ denotes a value of a corresponding j-th pixel in a spatial sensitivity map containing the attenuation information of the subject.

Figure 10A:
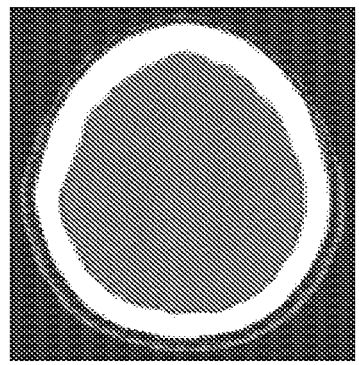
FIGS. 10A and 10B illustrate a CT image and a PET image of the brain of the subject according to some embodiments of the present disclosure.
Figure 10B:
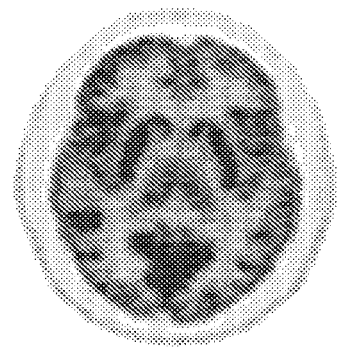
Figure 10C:
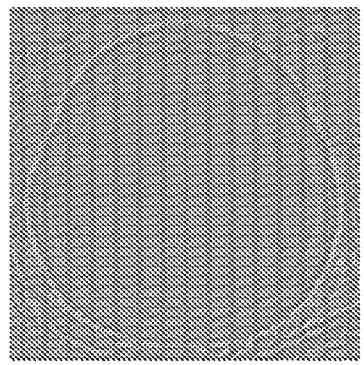
FIGS. 10C and 10D illustrate boundaries of the brain identified from the CT image and the PET image according to some embodiments of the present disclosure.
Figure 10D:
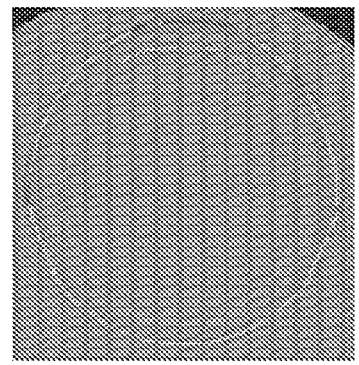

In some embodiments, boundary information of structures of the subject may be determined from one or more images of the subject. In some embodiments, the boundary information of the subject may be determined by identifying boundaries of anatomical structures of the subject from the one or more images. The one or more images may include a CT image, an MR image, a PET image (e.g., the preliminary image), etc. In some embodiments, the boundaries may be identified from the one or more images using an image segmentation algorithm, such as a threshold-based segmentation algorithm, a region-based segmentation algorithm, a neural network based segmentation algorithm, etc. Illustratively, a CT image and a PET image of the brain of the subject may be illustrated in FIGS. 10A and 10B, respectively. Boundaries of the brain may be identified from the CT image and the PET image using an image segmentation algorithm. The boundaries of the brain identified from the CT image and the PET image may be illustrated in FIGS. 10C and 10D, respectively.

Merely by way of example, extracted boundaries of structures in a CT image may be expressed as Formula (34):

$$e_j = \left| 0.5 - \left( \sum_{i \in B} \left( \frac{1}{f_i / f_j + 1} \right) - 0.5 \right) / N_B \right|, \quad (34)$$

where $e_j$ denotes a value of a j-th pixel on a boundary in the CT image, B denotes a neighborhood (i.e., a region centered by the j-th pixel) of the j-th pixel in the CT image, $f_i$ denotes a value of an i-th pixel in the CT image, $i \in B$, and $N_B$ denotes the number or count of pixels in the neighborhood.

In some embodiments, the regularization parameter may be determined according to Formula (35) considering the noise adjustment coefficient, the NEC, the spatial sensitivity of the PET scanner, the attenuation information of the subject, and boundary information of the subject:

$$\psi(e_j) = \begin{cases} 0.5 & e_j = 0 \\ e_j & e_j \neq 0 \end{cases}, \quad (35)$$

where $\Psi(e_j)$ denotes boundary information of structures of the subject.

In some embodiments, the regularization parameter may be determined according to Formula (36) considering the noise adjustment coefficient, the NEC, the spatial sensitivity of the PET scanner, and the attenuation information of the subject:

$$\beta_j = a \cdot (NEC)^{(-0.3)} \cdot \frac{1}{\sqrt{\text{sns\_map}_j}} \cdot \psi(e_j). \qquad (36)$$

In some embodiments, the image reconstruction process may include a plurality of iterations. In each of the plurality of iterations, a PET image reconstructed in a prior iteration may be updated based on the objective function configured with the regularization parameter. In some embodiments, the boundary information of structures of the subject may be updated based on a reconstructed PET image in each iteration. In this case, the regularization parameter may also be updated in the plurality of iterations.

In some embodiments, a CT image or an MR image of the subject may be obtained. Both the boundary information of structures and the attenuation information of the subject may be determined based on the CT image or the MR image. In some embodiments, the CT image or the MR image may be obtained before the image reconstruction is initiated so as to speed up the image reconstruction process.

In some embodiments, the attenuation information of the subject may be determined based on the CT image or the MR image. The boundary information of structures of the subject may be determined based on a preliminary image. In some embodiments, the CT image or the MR image, and the preliminary image may be obtained before the image reconstruction is initiated so as to speed up the image reconstruction process.

Figure 11:
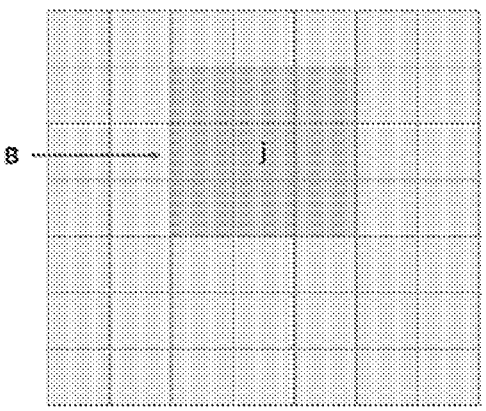
FIG. 11 illustrates a neighborhood of a certain size centered at a selected pixel according to some embodiments of the present disclosure.

In some embodiments, the boundary information of structures of the subject may be determined based on the preliminary image. For each pixel in the preliminary image, neighboring pixels within a neighborhood of the pixel may be determined. For example, for a selected pixel in the preliminary image, a neighborhood of a certain size (e.g., 3×3 pixels as illustrated in FIG. 11, 5×5 pixels, etc.) centered at the selected pixel may be determined. Pixels around the selected pixels within the neighborhood of the selected pixel may be determined as neighboring pixels. Values of the neighboring pixels may be obtained. In some embodiments, the boundary information of structures of the subject may be determined according to a pixel value of the selected pixel, pixel values of the neighboring pixels in the neighborhood of the pixel, and the number of the neighboring pixels. In some embodiments, the boundary information may be determined using differences in pixel values and the number or count of pixels between each pixel and its corresponding neighboring pixels in the preliminary image, which may accurately reflect the boundaries of structures of the subject. It should be noted that the determination of the boundary information of the subject based on the preliminary image is merely for illustration purposes, which may also be applicable to the calculation of the boundary information based on a CT image or an MR image.

It should be noted that the above description regarding the regularization parameter is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, the one or more other components of the regularization parameter may include one or more global factors that relate to at least one of the denoised image or the subject. The noise adjustment coefficient may be one of the global factors. In some embodiments, the global factors may further include a general parameter of the subject. Merely by way of example, the general parameter of the subject may include the level of obesity, the age, the weight, etc. of the subject.

Figure 12:
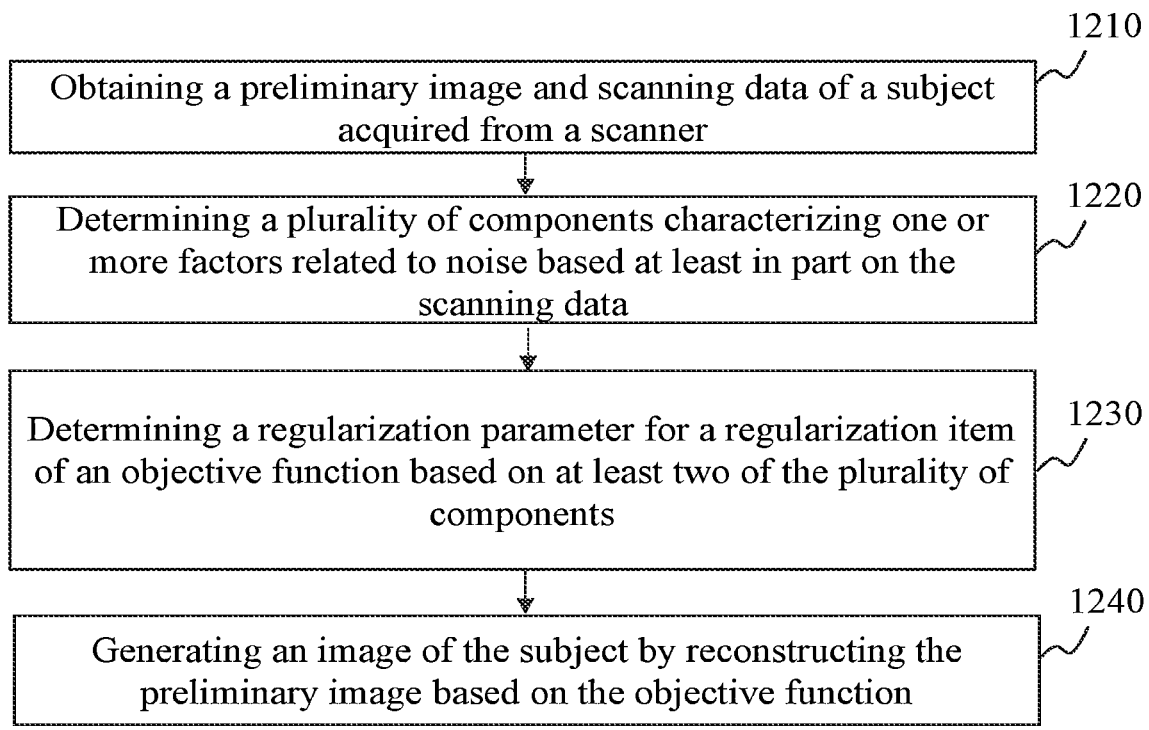
FIG. 12 includes a flowchart illustrating an exemplary process for generating a denoised image according to some embodiments of the present disclosure.

FIG. 12 includes a flowchart illustrating an exemplary process for generating a denoised image according to some embodiments of the present disclosure. In some embodiments, at least a portion of the process 1200 may be performed by the processing device 120 (e.g., implemented in the computing apparatus 200 shown in FIG. 2, the processing device illustrated in FIG. 4). In some embodiments, at least a portion of the process 1200 may be performed by a terminal device (e.g., the mobile device 300 shown in FIG. 3) embodying software and/or hardware.

In 1210, a preliminary image and scanning data of a subject acquired from a scanner may be obtained. In some embodiments, the preliminary image and the scanning data may be obtained by obtaining module 410.

The scanning data may be generated by scanning the subject using the scanner. In some embodiments, the scanner may be implemented by the imaging scanner 110. The imaging scanner 110 may be, for example, a PET scanner, a CT scanner, an ECT scanner, a SPECT scanner, etc.

In some embodiments, the preliminary image may be generated by reconstructing the scanning data of the subject using a reconstruction algorithm. Any suitable image reconstruction algorithms may be employed according to a type of the preliminary image (e.g., a CT image, a PET image, an ECT image, etc.). In some embodiments, the preliminary image may be any image suitable for iterative reconstruction. In some embodiments, the preliminary image may be an image stored in a storage device (e.g., the storage device 130, the storage 220, etc.) of the imaging system 100. In some embodiments, the operation 1210 may be similar to or the same as the operation 510 of the process 500 as illustrated in FIG. 5.

In 1220, a plurality of components characterizing one or more factors related to noise may be determined based at least in part on the scanning data. In some embodiments, the plurality of components characterizing the one or more factors related to noise may be determined by the regularization module 420.

The one or more factors related to noise may be attributes or features of a condition under which the subject is scanned and/or an image of the subject is reconstructed. The attributes or features may influence a noise level and/or noise distribution in the image. Merely for illustration purposes, the one or more factors related to noise in an image may include the quality of the scanning data, a hardware and/or software configurations, scanning parameters, etc. of the imaging scanner 110, one or more features of the subject (e.g., attenuation information, boundary information of anatomical structures, the level of obesity of the subject, the age of the subject, the weight of the subject, etc.), a scanning condition (e.g., a dose of the radionuclide administered into the subject), etc. The plurality of components may characterize the one or more factors. In some embodiments, the plurality of components may include at least one component characterizing the quality of the scanning data (referred to as "first component" for brevity), at least one component characterizing the imaging scanner 110 (referred to as "second component" for brevity), at least one component characterizing features of the subject (referred to as "third component" for brevity), and one or more additional components.

In some embodiments, the at least one first component may relate to an NEC. The at least one second component may relate to a spatial sensitivity of the PET scanner. The at least one third component may relate to attenuation information and/or boundary information of anatomical structures of the subject. The additional components may include a noise adjustment coefficient and a general parameter of the subject. The noise adjustment coefficient may adjust an overall noise level of the image. The general parameter of the subject may include the level of obesity, the age, the weight, etc., of the subject.

In some embodiments, the at least one first component related to the NEC, the at least one second component related to spatial sensitivity of the PET scanner may be determined based on the scanning data. In some embodiments, a third component relating to attenuation information of the subject may be determined based on the scanning data, and a CT image or an MR image. Another third component relating to boundary information of anatomical structures of the subject may be determined based on the scanning data, and a CT image, an MR image, or a PET image (e.g., the preliminary image).

In 1230, a regularization parameter for a regularization item of an objective function may be determined based on at least two of the plurality of components. In some embodiments, the plurality of components characterizing the one or more factors related to noise may be determined by the regularization module 420.

In some embodiments, the regularization parameter may be determined based on the plurality of components according to Formula (36). In some embodiments, the regularization parameter may be determined based on at least two of the at least one first component, the at least one second component, or the at least one third component. For example, the regularization parameter may be determined based on the at least one first component and the at least one second component according to Formula (31). As another example, the regularization parameter may be determined based on the at least one first component and a third component relate to boundary information of anatomical structures of the subject according to Formula (37):

$$\beta = a \cdot (NEC)^{-0.3} \cdot \Psi(e_j). \quad (37)$$

In 1240, an image of the subject may be generated by reconstructing the preliminary image based on the objective function. In some embodiments, the image of the subject may be generated by the reconstruction module 430. The objective function configured with the regularization parameter may be employed in the iterative image reconstruction process, thereby improving the quality of the image. In some embodiments, the operation 1240 may be similar to or the same as the operation 530 of the process 500 as illustrated in FIG. 5.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device including a set of instructions; and
at least one processor configured to communicate with the at least one storage device, wherein when executing the set of instructions, the at least one processor is configured to direct the system to perform operations including:
obtaining a preliminary image and scanning data of a subject acquired using a scanner;
determining a regularization parameter for a regularization item of an objective function based at least in part on the scanning data, wherein the regularization parameter includes a component characterizing a feature of the subject; and
generating an image of the subject by reconstructing the preliminary image based on the objective function, wherein the component of the regularization parameter relates to attenuation information and boundary information of the subject, and the attenuation information is combined with a spatial sensitivity of the scanner via a spatial sensitivity map that includes the spatial sensitivity of the scanner and the attenuation information of the subject.

2. The system of claim 1, wherein the scanning data includes at least one of positron emission tomography (PET) data, computed tomography (CT) data, emission computed tomography (ECT) data, or single-photon emission computed tomography (SPECT) data.

3. The system of claim 1, wherein the attenuation information is determined based on a CT image or a magnetic resonance (MR) image of the subject.

4. The system of claim 1, wherein the boundary information of the subject is determined based on a CT image, an MR image, or the preliminary image.

5. The system of claim 1, wherein the regularization parameter further includes one or more global factors that relates to at least one of the image or the subject.

6. The system of claim 5, wherein one of the one or more global factors includes a noise adjustment coefficient for adjusting a noise level of the image.

7. The system of claim 5, wherein one of the one or more global factors includes a general parameter of the subject.

8. The system of claim 1, wherein the objective function includes at least one of a total variation function, a quadratic function, or a Huber function.

9. The system of claim 1, wherein the regularization parameter further includes a second component characterizing the quality of the scanning data.

10. The system of claim 9, wherein the scanning data is PET data, and the second component relates to a noise equivalent counts relating to the PET data.

11. The system of claim 1, wherein the regularization parameter further includes a third component characterizing the scanner.

12. The system of claim 11, wherein the third component relates to a plurality of sensitivity values of the spatial sensitivity of the scanner.

13. The system of claim 12, wherein the scanning data is PET data, and each of the plurality of sensitivity values relate to the PET data corresponding a point in a scanning region of the scanner.

14. The system of claim 1, wherein the regularization parameter further includes a fourth component relating to a portion of the preliminary image.

15. The system of claim 14, wherein the portion of the preliminary image includes one or more regions including one or more pixels or voxels that satisfy a criterion in the preliminary image.

16. A method implemented on a computing device having a processor and a computer-readable storage device, the method comprising:
- obtaining a preliminary image and scanning data of a subject acquired using a scanner;
- determining a regularization parameter for a regularization item of an objective function based at least in part on the scanning data, wherein the regularization parameter includes a component characterizing a feature of the subject; and
- generating an image of the subject by reconstructing the preliminary image based on the objective function, wherein the component of the regularization parameter relates to attenuation information and boundary information of the subject, and the attenuation information is combined with a spatial sensitivity of the scanner via a spatial sensitivity map that includes the spatial sensitivity of the scanner and the attenuation information of the subject.

17. The method of claim 16, wherein the regularization parameter further includes a second component characterizing the quality of the scanning data.

18. The method of claim 17, wherein the scanning data is PET data, and the second component relates to a noise equivalent counts relating to the PET data.

19. The method of claim 16, wherein the regularization parameter further includes a third component characterizing the scanner.

20. The method of claim 19, wherein the third component relates to a plurality of sensitivity values of the spatial sensitivity of the scanner.

* * * * *